United States Patent
Mustoe et al.

(10) Patent No.: US 11,065,262 B2
(45) Date of Patent: Jul. 20, 2021

(54) TOPICAL TREATMENT OF WOUNDS WITH STATINS AND CHOLESTEROL FOR SCAR REDUCTION

(71) Applicant: Northwestern University, Evanston, IL (US)

(72) Inventors: Thomas A. Mustoe, Evanston, IL (US); Robert D. Galiano, Chicago, IL (US); Seok Jong Hong, Northbrook, IL (US); Ping Xie, Chicago, IL (US); Shengxian Jia, Wilmette, IL (US)

(73) Assignee: Northwestern University, Evanston, IL (US)

( * ) Notice: Subject to any disclaimer, the term of this patent is extended or adjusted under 35 U.S.C. 154(b) by 28 days.

(21) Appl. No.: 16/047,464

(22) Filed: Jul. 27, 2018

(65) Prior Publication Data

US 2019/0030045 A1    Jan. 31, 2019

Related U.S. Application Data

(60) Provisional application No. 62/537,534, filed on Jul. 27, 2017.

(51) Int. Cl.
| | |
|---|---|
| A61K 31/575 | (2006.01) |
| A61K 31/225 | (2006.01) |
| A61K 9/107 | (2006.01) |
| A61K 47/14 | (2017.01) |
| A61K 47/10 | (2017.01) |
| A61K 31/366 | (2006.01) |
| A61K 9/06 | (2006.01) |
| A61K 9/14 | (2006.01) |
| A61K 47/44 | (2017.01) |
| A61K 9/00 | (2006.01) |
| A61P 17/02 | (2006.01) |
| A61K 47/12 | (2006.01) |
| A61K 31/22 | (2006.01) |
| A61K 45/06 | (2006.01) |

(52) U.S. Cl.
CPC .......... *A61K 31/575* (2013.01); *A61K 9/0014* (2013.01); *A61K 9/06* (2013.01); *A61K 9/107* (2013.01); *A61K 9/1075* (2013.01); *A61K 9/14* (2013.01); *A61K 31/22* (2013.01); *A61K 31/225* (2013.01); *A61K 31/366* (2013.01); *A61K 45/06* (2013.01); *A61K 47/10* (2013.01); *A61K 47/12* (2013.01); *A61K 47/14* (2013.01); *A61K 47/44* (2013.01); *A61P 17/02* (2018.01)

(58) Field of Classification Search
CPC ...... A61K 31/575; A61K 9/0014; A61K 9/06; A61K 9/107; A61K 9/1075; A61K 9/14; A61K 31/22; A61K 31/225; A61K 31/366; A61K 45/06; A61K 47/10; A61K 47/12; A61K 47/14; A61K 47/44; A61P 17/02

See application file for complete search history.

(56) References Cited

U.S. PATENT DOCUMENTS

| | | | |
|---|---|---|---|
| 7,101,907 B2 | 9/2006 | Gasper | |
| 2011/0091552 A1* | 4/2011 | McCaffrey | A61K 31/04 424/484 |
| 2011/0105966 A1* | 5/2011 | Kazerooni | A61H 3/008 601/35 |
| 2011/0105996 A1* | 5/2011 | Mustoe | A61K 31/25 604/20 |
| 2011/0165203 A1* | 7/2011 | Bouwstra | A61K 47/44 424/400 |

OTHER PUBLICATIONS

Suzuki-Banhesse (Year: 2014).*
Alinaghi et al., Impact of solidification on the performance of lipid-based colloidal carriers: oil-based versus self-emulsifying systems. Curr Drug Deliv. 2015;12(1):16-25.
Asai et al., Topical simvastatin accelerates wound healing in diabetes by enhancing angiogenesis and lymphangiogenesis. Am J Pathol. Dec. 2012;181(6):2217-24.
Bitto et al., Simvastatin enhances VEGF production and ameliorates impaired wound healing in experimental diabetes. Pharmacol Res. Feb. 2008;57(2):159-69.
Brazzelli et al., Effects of systemic treatment with statins on skin barrier function and stratum corneum water-holding capacity. Dermatology. 1996;192(3):214-6.
Cho et al., Development of udenafil-loaded microemulsions for intranasal delivery: in vitro and in vivo evaluations. Int J Pharm. Feb. 28, 2012;423(2):153-60.
Dahan et al., The solubility-permeability interplay and its implications in formulation design and development for poorly soluble drugs. AAPS J. Jun. 2012;14(2):244-51.
Duangjit et al., Application of Design Expert for the investigation of capsaicin-loaded microemulsions for transdermal delivery. Pharm Dev Technol. Sep. 2016;21(6):698-705.
Eberlein et al., Rho-dependent inhibition of the induction of connective tissue growth factor (CTGF) by HMG CoA reductase inhibitors (statins). Br J Pharmacol. Aug. 2001;133(7):1172-80.
Elnaggar et al., Lecithin-based nanostructured gels for skin delivery: an update on state of art and recent applications. J Control Release. Apr. 28, 2014;180:10-24.
Evangelista et al., Simvastatin as a novel therapeutic agent for venous ulcers: a randomized, double-blind, placebo-controlled trial. Br J Dermatol. May 2014;170(5):1151-7.
Farsaei et al., Potential role of statins on wound healing: review of the literature. Int Wound J. Jun. 2012;9(3):238-47.
Feingold et al., Cholesterol synthesis is required for cutaneous barrier function in mice. J Clin Invest. Nov. 1990;86(5):1738-45.
Feingold et al., The lovastatin-treated rodent: a new model of barrier disruption and epidermal hyperplasia. J Invest Dermatol. Feb. 1991;96(2):201-9.

(Continued)

*Primary Examiner* — Jeffrey S Lundgren
*Assistant Examiner* — Ibrahim D Bori
(74) *Attorney, Agent, or Firm* — Casimir Jones SC; David W. Staple

(57) ABSTRACT

Provided herein are compositions, systems, and methods for treating wounds with the combination of statins and cholesterol to help prevent and reduce scar formation.

14 Claims, 11 Drawing Sheets

Specification includes a Sequence Listing.

(56) References Cited

OTHER PUBLICATIONS

Finnin et al., Transdermal penetration enhancers: applications, limitations, and potential. J Pharm Sci. Oct. 1999;88(10):955-8.
Fitzmaurice et al., Do statins have a role in the promotion of postoperative wound healing in cardiac surgical patients? Ann Thorac Surg. Aug. 2014;98(2):756-64.
Fukami et al., Effects of HMG-CoA reductase inhibitors on skeletal muscles of rabbits. Res Exp Med (Berl). 1993;193(5):263-73.
Fulmer et al., Stratum corneum lipid abnormalities in surfactant-induced dry scaly skin. J Invest Dermatol. May 1986;86(5):598-602.
Germershausen et al., Tissue selectivity of the cholesterol-lowering agents lovastatin, simvastatin and pravastatin in rats in vivo. Biochem Biophys Res Commun. Feb. 15, 1989;158(3):667-75.
Goyal et al., Formulation design and evaluation of a self-microemulsifying drug delivery system of lovastatin. Acta Pharm. Nov. 2012;62(3):357-70.
Gurtner et al., Improving cutaneous scar formation by controlling the mechanical environment: large animal and phase I studies. Ann Surg. Aug. 2011;254(2):217-25.
Hughes et al., A comparison between the effects of hydrophobic and hydrophilic statins on osteoclast function in vitro and ovariectomy-induced bone loss in vivo. Calcif Tissue Int. Nov. 2007;81(5):403-13.
Ichihara et al., Disparity between angiographic regression and clinical event rates with hydrophobic statins. Lancet. Jun. 22, 2002;359(9324):2195-8.
Inugala et al., Solid self-nanoemulsifying drug delivery system (S-SNEDDS) of darunavir for improved dissolution and oral bioavailability: In vitro and in vivo evaluation. Eur J Pharm Sci. Jul. 10, 2015;74:1-10.
Jia et al., Intravenous curcumin efficacy on healing and scar formation in rabbit ear wounds under nonischemic, ischemic, and ischemia-reperfusion conditions. Wound Repair Regen. Nov.-Dec. 2014;22(6):730-9.
Jowkar et al., Statins in dermatology. International journal of dermatology 2010;49:1235-43.
Ko et al., HMG-CoA reductase inhibitors (statins) reduce hypertrophic scar formation in a rabbit ear wounding model. Plast Reconstr Surg. Feb. 2012;129(2):252e-261e.
Kogan et al., Microemulsions as transdermal drug delivery vehicles. Adv Colloid Interface Sci. Nov. 16, 2006;123-126:369-85.
Laing et al., Effect of pravastatin on experimental diabetic wound healing. J Surg Res. Jun. 15, 2010;161(2):336-40.
Lawrence et al., Microemulsion-based media as novel drug delivery systems. Adv Drug Deliv Rev. Dec. 6, 2000;45(1):89-121.
Leask et al., Insights into the molecular mechanism of chronic fibrosis: the role of connective tissue growth factor in scleroderma. J Invest Dermatol. Jan. 2004;122(1):1-6.
Lee et al., Enhanced topical delivery of tacrolimus by a carbomer hydrogel formulation with transcutol P. Drug Dev Ind Pharm. Oct. 2016; 42(10):1636-42.
Menon et al., Structural basis for the barrier abnormality following inhibition of HMG CoA reductase in murine epidermis. J Invest Dermatol. Feb. 1992;98(2):209-1.
Meyer-Ter-Vehn et al., Lovastatin inhibits TGF-beta-induced myofibroblast transdifferentiation in human tenon fibroblasts. Invest Ophthalmol Vis Sci. Sep. 2008;49(9):3955-60.
Mostafa et al., Transdermal microemulsions of *Boswellia carterii* Bird: formulation, characterization and in vivo evaluation of anti-inflammatory activity. Drug Deliv. 2015;22(6):748-56.
Mun et al., Simvastatin inhibits transforming growth factor-beta1-induced expression of type I collagen, CTGF, and alpha-SMA in keloid fibroblasts. Wound Repair Regen. Jan.-Feb. 2014;22(1):125-33.
Murota et al., Topical cholesterol treatment ameliorates hapten-evoked cutaneous hypersensitivity by sustaining expression of 11beta-HSD1 in epidermis. Exp Dermatol. Jan. 2014;23(1):68-70.
Murtaza, Solubility enhancement of simvastatin: a review. Acta Pol Pharm. Jul.-Aug. 2012;69(4):581-90.
Mustoe et al., Growth factor-induced acceleration of tissue repair through direct and inductive activities in a rabbit dermal ulcer model. J Clin Invest. Feb. 1991;87(2):694-703.
Mustoe et al., International clinical recommendations on scar management. Plast Reconstr Surg. Aug. 2002;110(2):560-71.
O'Shaughnessy et al., Homeostasis of the epidermal barrier layer: a theory of how occlusion reduces hypertrophic scarring. Wound Repair Regen. Sep.-Oct. 2009;17(5):700-8.
Paller et al., Pathogenesis-based therapy reverses cutaneous abnormalities in an inherited disorder of distal cholesterol metabolism. J Invest Dermatol. Nov. 2011;131(11):2242-8.
Pathak et al., Role of mucoadhesive polymers in enhancing delivery of nimodipine microemulsion to brain via intranasal route. Acta Pharm Sin B. Apr. 2014;4(2):151-60.
Petyaev, Improvement of hepatic bioavailability as a new step for the future of statin. Arch Med Sci. Apr. 25, 2015;11(2):406-10.
Pund et al., Multivariate analysis of physicochemical characteristics of lipid based nanoemulsifying cilostazol—quality by design. Colloids Surf B Biointerfaces. Mar. 1, 2014;115:29-36.
Rajpoot et al., Anticancer efficacy, tissue distribution and blood pharmacokinetics of surface modified nanocarrier containing melphalan. Int J Pharm. Apr. 15, 2012;426(1-2):219-230.
Rego et al., Simvastatin improves the healing of infected skin wounds of rats. Acta Cir Bras. Mar.-Apr. 2007;22 Suppl 1:57-63.
Schmalfuss et al., Modification of drug penetration into human skin using microemulsions. Journal of Controlled Release 1997;46:279-85.
Shah et al., Preclinical formulations: insight, strategies, and practical considerations. AAPS PharmSciTech. Oct. 2014;15(5):1307-23.
Shang et al., Simvastatin downregulates expression of TGF-betaRII and inhibits proliferation of A549 cells via ERK. Tumour Biol. Jun. 2015;36(6):4819-24.
Sidgwick et al., A comprehensive evidence-based review on the role of topicals and dressings in the management of skin scarring. Arch Dermatol Res. Aug. 2015;307(6):461-77.
Sisco et al., Antisense inhibition of connective tissue growth factor (CTGF/CCN2) mRNA limits hypertrophic scarring without affecting wound healing in vivo. Wound Repair Regen. Sep.-Oct. 2008;16(5):661-73.
Solanki et al., Microemulsion drug delivery system: for bioavailability enhancement of ampelopsin. ISRN Pharm. 2012;2012:108164.
Subedi et al., Recent advances in transdermal drug delivery. Arch Pharm Res. Mar. 2010;33(3):339-51.
Sullivan et al., A review of the nonclinical safety of Transcutol(R), a highly purified form of diethylene glycol monoethyl ether (DEGEE) used as a pharmaceutical excipient. Food Chem Toxicol. Oct. 2014;72:40-50.
Suzuki-Banhesse et al., Effect of atorvastatin on wound healing in rats. Biol Res Nurs. Mar. 2015;17(2):159-68.
Toker et al., Topical atorvastatin in the treatment of diabetic wounds. Am J Med Sci. Sep. 2009;338(3):201-4.
Urbich et al., Double-edged role of statins in angiogenesis signaling. Circ Res. Apr. 5, 2002;90(6):737-44.
Vukelic et al., Farnesyl pyrophosphate inhibits epithelialization and wound healing through the glucocorticoid receptor. J Biol Chem. Jan. 15, 2010;285(3):1980-8.
Wang et al., Topical simvastatin promotes healing of *Staphylococcus aureus*-contaminated cutaneous wounds. Int Wound J. Dec. 2016;13(6):1150-1157.
Watts et al., Connective tissue growth factor expression and induction by transforming growth factor-beta is abrogated by simvastatin via a Rho signaling mechanism. Am J Physiol Lung Cell Mol Physiol. Dec. 2004;287(6):L1323-32.
Watts et al., RhoA signaling modulates cyclin D1 expression in human lung fibroblasts; implications for idiopathic pulmonary fibrosis. Respir Res. Jun. 15, 2006;7:88.
Watts et al., Simvastatin inhibits growth factor expression and modulates profibrogenic markers in lung fibroblasts. Am J Respir Cell Mol Biol. Apr. 2005;32(4):290-300.
Weis et al., Statins have biphasic effects on angiogenesis. Circulation. Feb. 12, 2002;105(6):739-45.

(56) References Cited

OTHER PUBLICATIONS

Yadav et al., Development, characterization, and pharmacodynamic evaluation of hydrochlorothiazide loaded self-nanoemulsifying drug delivery systems. ScientificWorldJournal. 2014;2014:274823.

Zhu et al., Disparate effects of simvastatin on angiogenesis during hypoxia and inflammation. Life Sci. Dec. 5, 2008;83(23-24):801-9.

\* cited by examiner

TOPICAL TREATMENT OF WOUNDS WITH STATINS AND CHOLESTEROL FOR SCAR REDUCTION

The present application claims priority to U.S. Provisional application Ser. No. 62/537,534, filed Jul. 27, 2017, which is herein incorporated by reference in its entirety.

STATEMENT REGARDING FEDERAL FUNDING

This invention was made with government support under W81XWH-13-2-0052 awarded by the U.S. Army Medical Research and Materiel Command. The government has certain rights in the invention.

FIELD OF THE INVENTION

Provided herein are compositions, systems, and methods for treating wounds with the combination of statins and cholesterol to help prevent and reduce scar formation.

BACKGROUND

Hypertrophic scar is frequently the sequel of burns and other traumatic injuries with significant cosmetic and functional consequences, especially when it is in the face and across joints. There are limited therapeutic options for the reduction of scarring following these injuries beyond promotion of re-epithelialization and control of inflammation. Available chemotherapeutic options with solid evidence of clinical efficacy are limited to topical silicone gel and intralesional steroid injections, each with major limitations (1,2). Mechanical manipulation to reduce tension in surgical incisions can improve scar outcome (3), but are not practical for burn scars or large post traumatic injuries. It is unlikely that any single therapy will be sufficient to produce optimal scar outcomes. Therefore, there is great need for new, efficacious therapeutic options that can be delivered alone or in conjunction with current therapies through local route with minimal toxicity or impairment of healing. Scarring has multifactorial etiologies, so optimal treatment may involve combination of multi-treatment modalities such as topical agent mixed with silicone gel, etc.

Administration of pharmaceutical agents by intradermal injection is a challenging treatment modality, which is painful, and requires a health care professional. Comparing to intradermal injection, topical application has many advantages such as ease of handling, the localized delivery of product and the reduced effect of first pass metabolism etc (5). Furthermore, a suitable concentration of reagent(s) can be applied topically without a risk of systemic effects (6). However, a major difficulty in topical administration is adequate transdermal delivery, which requires both high solubility and penetration capability of topical agents.

SUMMARY

Provided herein are compositions, systems, and methods for treating wounds with the combination of statins and cholesterol to help prevent and reduce scar formation.

In some embodiments, provided herein are methods of preventing or reducing scar formation in the skin of a subject during would healing comprising: administering a composition topically to a wound site of a subject (e.g., a human, or animal) such that scar tissue formation in the skin is reduced or prevented during would healing, wherein the composition comprises: i) a statin at a concentration of 20-500 µM (e.g., 20 . . . 30 . . . 40 . . . 50 . . . 60 . . . 100 . . . 125 . . . 150 . . . 175 . . . 200 . . . 225 . . . 250 . . . 275 . . . 300 . . . 325 . . . 350 . . . 375 . . . 400 . . . 425 . . . 450 . . . 475 . . . or 500 µM) and/or a percentage of 1-25% (e.g., 1 . . . 5 . . . 10 . . . 15 . . . 20 . . . or 25%) of the pharmaceutically acceptable carrier, and ii) cholesterol, cholesterol derivative, or cholesterol analog at 1-15% (e.g., 1 . . . 3 . . . 5 . . . 7 . . . 10 . . . 12 . . . 14 or 15%) of the pharmaceutically acceptable carrier.

In certain embodiments, provided herein are compositions comprising: a) a statin at a concentration of 20-500 µM (e.g., 20 . . . 30 . . . 40 . . . 50 . . . 60 . . . 100 . . . 125 . . . 150 . . . 175 . . . 200 . . . 225 . . . 250 . . . 275 . . . 300 . . . 325 . . . 350 . . . 375 . . . 400 . . . 425 . . . 450 . . . 475 . . . or 500 µM) and/or a percentage of 1-25% (e.g., 1 . . . 5 . . . 10 . . . 15 . . . 20 . . . or 25%) of the pharmaceutically acceptable carrier, and b) cholesterol, cholesterol derivative, or cholesterol analog at 1-15% (e.g., 1 . . . 3 . . . 5 . . . 7 . . . 10 . . . 12 . . . 14 or 15%) of the pharmaceutically acceptable carrier.

In particular embodiments, provided herein are systems comprising: a) a composition comprising: i) a statin at a concentration of 20-500 µM (e.g., 20 . . . 30 . . . 40 . . . 50 . . . 60 . . . 100 . . . 125 . . . 150 . . . 175 . . . 200 . . . 225 . . . 250 . . . 275 . . . 300 . . . 325 . . . 350 . . . 375 . . . 400 . . . 425 . . . 450 . . . 475 . . . or 500 µM) and/or a percentage of 1-25% (e.g., 1 . . . 5 . . . 10 . . . 15 . . . 20 . . . or 25%) of the pharmaceutically acceptable carrier, and ii) cholesterol, cholesterol derivative, or cholesterol analog at 1-15% (e.g., 1 . . . 3 . . . 5 . . . 7 . . . 10 . . . 12 . . . 14 or 15%) of the pharmaceutically acceptable carrier; and b) a delivery component selected from: i) a wound dressing, or ii) a topical composition applicator device, wherein the composition is present in at least part of the wound dressing or located inside the topical applicator device. In certain embodiments, the wound dressing comprises a sterile pad, wherein at least a portion of the composition is present in the sterile pad. In other embodiments, the topical composition applicator device comprises a spray bottle or a tube with dispensing tip.

In some embodiments, the composition further comprises a pharmaceutically acceptable carrier. In certain embodiments, the cholesterol derivative is a cholesterol ester. In particular embodiments, the cholesterol ester is selected from the group consisting of: cholesteryl capronate, cholesteryl pelargonate, cholesteryl caprinate, cholesteryl undecilate, cholesteryl laurate, cholesteryl tridecilate, cholesteryl miristinate, cholesteryl palmitate, and cholesteryl stearate. In further embodiments, the cholesterol analog is selected from the group consisting of: sitosterol, stigmasterol, fucosterol, spinasterol, campesterol, brassicasterol and ergosterol. In certain embodiments, the cholesterol, cholesterol derivative, or cholesterol analog is present at 2-10% in the composition.

In particular embodiments, the statin is selected from the group consisting of: simvastatin, rosuvastatin, lovastatin, cerivastatin, fluvastatin, mevastatin, pitavastatin, and pravastatin. In some embodiments, the statin has molecular weight less than 500 daltons (e.g., 499-400 daltons, or 300-399 daltons). In some embodiments, the wound site comprises at least some scar tissue. In further embodiments, the statin is present at: i) a concentration of 45 to 150 µM or a percentage of 2-5% of the composition, or ii) a concentration of 225-400 µM (e.g., 235 . . . 255 µM) or a percentage of 8-20% (e.g., 9-11%) of the composition.

In certain embodiments, the composition comprises an emulsion. In particular embodiments, the emulsion comprises an microemulsion, and wherein the microemulsion comprises an oil phase, a first surfactant (e.g., a non-ionic surfactant), a second surfactant, and an oil phase. In further embodiments, the emulsion comprises an oil-in-water emulsion. In other embodiments, the emulsion comprises a water-in-oil emulsion. In additional embodiments, the emulsion comprises a surfactant (e.g., non-ionic surfactant) and a solvent. In other embodiments, the surfactant comprises monoacylglycerols. In other embodiments, the solvent is selected from the group consisting of: water polyethylene glycol, oleic acid, and 2-(2-ethoxyethoxy) ethanol.

In particular embodiments, the methods further comprise repeating, at least once, the administering on the same day as the administering. In particular embodiments, the compositions are administered at least two, three, four, five or six times on the same day. In other embodiments, the administration (at least once, twice . . . six times per day) happens for at least one week (e.g., one week, two weeks, three weeks, four weeks, or five weeks). In some embodiments, the administration occurs twice a day. In some embodiments, the administration occurs once a day. In some embodiments, the administration occurs once every two days. In some embodiments, the administration occurs once every three days. In some embodiments, the administration occurs once every four days. In some embodiments, the administration occurs once every five days. In some embodiments, the administration occurs once every week. In certain embodiments, the composition comprises a form selected from the group consisting of: a powder, a spray, an ointment, a paste, a cream, a lotion, and a gel. In other embodiments, the composition comprises vegetable oil. In some embodiments, the wound site comprises scar tissue. In some embodiments, the wound site does not comprise scar tissue.

DEFINITIONS

Figure 1:
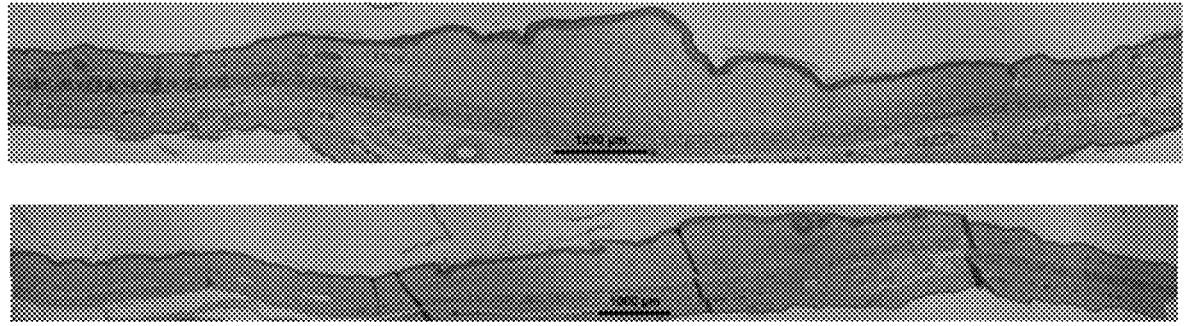
FIG. 1. Pravastatin intradermal administration (lower picture) improved hypertrophic scarring significantly when comparing to saline control (upper picture). Representative histological pictures are shown. Bar is 1000 µm in length.

To facilitate an understanding of the present technology, a number of terms and phrases are defined below:

As used herein, "a" or "an" or "the" can mean one or more than one. For example, "a" cell can mean one cell or a plurality of cells.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "wound" refers broadly to injuries to tissue including the skin and subcutaneous tissue initiated in different ways, for example, by surgery, (e.g., incision sites, open post-cancer resection wounds, including but not limited to, removal of melanoma and breast cancer, etc.), contained post-operative surgical wounds, pressure sores (e.g., from extended bed rest), and wounds induced by trauma. As used herein, the term "wound" is used without limitation to the cause of the wound, be it a physical cause such as bodily positioning as in bed sores, impact as with trauma, or a biological cause such as disease process, aging process, obstetric process, or any other manner of biological process. Wounds caused by pressure may also be classified into one of four grades depending on the depth of the wound: Grade I wounds are limited to the epidermis; Grade II wounds extend into the dermis; Grade III wounds extend into the subcutaneous tissue; and Grade IV wounds expose bone (e.g., a bony pressure point such as the greater trochanter or the sacrum). The term "partial thickness wound" refers to wounds that are limited to the epidermis and dermis; a wound of any etiology may be partial thickness. The term "full thickness wound" is meant to include wounds that extend through the dermis.

As used herein, "wound site" refers broadly to the anatomical location of a wound, without limitation.

As used herein, the term "chronic wound" refers to a wound that has not healed within 30 days.

As used herein, the term "dressing" refers broadly to any material applied to a wound for protection, absorbance, drainage, treatment, etc. Numerous types of dressings are commercially available, including films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (nonwoven composites of fibers from calcium alginate), and cellophane (cellulose with a plasticizer) (Kannon and Garrett (1995) *Dermatol. Surg.* 21: 583-590; Davies (1983) *Burns* 10: 94; both of which are herein incorporated by reference). The present methods, systems, and compositions contemplate the use of dressings impregnated with statins and cholesterol, as well as with pharmacological compounds (e.g., antibiotics, antiseptics, thrombin, analgesic compounds, etc.). Cellular wound dressings include commercially available materials such as Apligraf®, Dermagraft®, Biobrane®, TransCyte®, Integra® Dermal Regeneration Template®, and OrCell®.

As used herein, the term "co-administration" refers to the administration of at least two agents (e.g., a statin and cholesterol as described herein) or therapies to a subject. In some embodiments, the co-administration of two or more agents or therapies is concurrent (e.g., statins and cholesterol or analog/derivative thereof are administered in the same composition or about the same time). In other embodiments, a first agent (e.g., statin or cholesterol or analog or derivative) is administered prior to a second agent or therapy (e.g., statin or cholesterol or analog or derivative).

As used herein, the term "pharmaceutically acceptable carrier" refers to any of the standard pharmaceutical carriers, such as a phosphate buffered saline solution, water, emulsions (e.g., such as oil/water or water/oil emulsions), and various types of wetting agents. The compositions also can include stabilizers and preservatives. For examples of carriers, stabilizers, and adjuvants, see, e.g., Martin, Remington's Pharmaceutical Sciences, 15th Ed., Mack Publ. Co., Easton, Pa. (1975).

DETAILED DESCRIPTION

Provided herein are compositions, systems, and methods for treating wounds with the combination of statins and cholesterol to help prevent and reduce scar formation.

In certain embodiments, cholesterol derivatives and/or analogs are used with the compositions, systems, and methods of the present disclosure. Cholesterol derivatives and analogs are known in the art, and are disclosed in U.S. Pat. Pub. 20130053357 and U.S. Pat. Pub. 20120041182, both of which are incorporated by reference as if fully set forth herein. Additional cholesterol derivatives include, for example, cholesteryl hemisuccinate, cholesteryl succinate, cholesteryl oleate, cholesteryl linoleate, cholesteryl eicosapentenoate, cholesteryl linolenate, cholesteryl arachidonate, cholesteryl palmitate, cholesteryl stearate, cholesteryl myristate, polyethylene glycol derivatives of cholesterol (cholesterol-PEG), water soluble cholesterol (for example, cholesterol methyl-β-cyclodextrin), coprostanol, cholestanol, or cholestane, cholic acid, cortisol, corticosterone or hydrocortisone and 7-dehydrocholesterol. In particular embodiments, the cholesterol derivative comprises a cholesterol ester. In certain embodiments, the cholester ester is selected from the group consisting of: cholesteryl capronate, cholesteryl pelargonate, cholesteryl caprinate, cholesteryl undecilate, cholesteryl laurate, cholesteryl tridecilate, cholesteryl miristinate, cholesteryl palmitate, and cholesteryl stearate. In some embodiments, the cholesterol analog is selected from the group consisting of: sitosterol, stigmasterol, fucosterol, spinasterol, campesterol, brassicasterol and ergosterol.

The methods, compositions, and systems disclosed herein employ at least one type of statin. Statins include, but are not limited to, Atorvastatin (brand names LIPITOR, TORVAST), Cerivastatin (brand names LIPOBAY, BAYCOL), Fluvastatin (brand names Lescol, Lecol XL), Lovastatin (brand names MEVACOR, ALTOCOR, ALTOPREY), Mevastatin (naturally occurring in organisms including, but not limited to, oyster mushrooms and *Monascus purpureus*), Pitavastatin (brand names LOVALO, PITAVA), Pravastatin (brand names PRAVACHOL, SELEKTINE, LIPOSTAT), Rosuvastatin (brand name CRESTOR), Simvastatin (brand names ZOCOR, LIPEX), Simvastatin+Ezetimibe combination therapy (brand name VYTORIN), Lovastatin+Niacin combination therapy (brand name ADVICOR), Atorystatin+Amlidipine combination therapy (brand name CADUET), and Simvastatin+Niacin combination therapy (brand name SIMCOR). The LDL-lowering potency varies between statin agents. Cerivastatin is the most potent, followed by (in order of decreasing potency), rosuvastatin, atorvastatin, simvastatin, lovastatin, pravastatin, and fluvastatin (Shepherd et al. (2003) *Am. J. Cardiol.* 91:11C-17C; herein incorporated by reference in its entirety). Statins can be sub-grouped according to their hydrophobicity or hydrophilicity. Pravastatin (Molecular weight (MW) 446 Da) and rosuvastatin (MW 500 Da) are hydrophilic while atorvastatin (MW 604 Da), cerivastatin (MW 481 Da), fluvastatin (MW 433 Da), lovastatin (MW 404 Da) and simvastatin (MW 418 Da) are hydrophobic. Hydrophobic statins easily diffuse through the cell membrane.

Compositions used in method embodiments of the present technology are pharmaceutically formulated for administration via topical administration. Such formulations, besides containing a statin and cholesterol or derivative or analog thereof, may comprise appropriate salts, buffers, solvents, dispersion media, antibacterial and antifungal agents, isotonic agents, and absorption delaying agents to render delivery of the composition in a stable manner and thus allow uptake by target tissues (e.g., epidermal tissue, scar tissue). Supplementary active ingredients may also be incorporated into the compositions. In certain embodiments, administration is localized to a wound and/or scar site or proximal to a wound and/or scar site.

Dosage forms for topical or transdermal administration of statins used in some method embodiments of the present technology include powders, sprays, ointments, pastes, creams, lotions, gels, solutions, and transdermal patches. The active component may be mixed under sterile conditions with a pharmaceutically-acceptable carrier or excipient, and with any preservatives or buffers that may be important. Powders and sprays can be prepared, for example, with excipients such as lactose, talc, silicic acid, aluminum hydroxide, calcium silicates, and polyamide powder, or mixtures of these substances. The ointments, pastes, creams, and gels may also contain excipients such as animal and vegetable fats, oils, waxes, paraffins, starch, tragacanth, mixtures of monoacylglycerols, propylene glycol, oleic acid, ethoxyethoxy ethanol, cellulose derivatives, polyethylene glycols, silicones, bentonites, silicic acid, talc and zinc oxide, or mixtures thereof.

Additional wound-active agents that may be used in combination methods in some embodiments provided herein include but are not limited to corticosteroids, interferon (IFN), 5-fluorouracil (5-FU), doxorubicin (Adriamycin), bleomycin, verapamil, retinoic acid, imiquimod, tamoxifen, tacrolimus, botulinum toxin, onion extract, hydrocortisone, silicone, vitamin E, TGF-beta (TGF-beta1, TGF-beta2, TGF-beta3), VEGF inhibitors, mannose-6-phosphate inhibitors, etanercept, recombinant human interleukin (rhIL-10), proline-cis-hydroxyproline, azetidine carboxylic acid, tranilast, pentoxifylline, anti-TGF agents (e.g., decorin), and Gentian violet.

In addition, the methods provided herein may be combined with other treatment methods for wounds and/or scars (e.g., hypertrophic scars, keloids), such methods including but not limited to occlusive dressings, compression therapy, cryosurgery, excision, radiation therapy, laser therapy, and phototherapy (e.g., photodynamic therapy, UVA-1 therapy, narrowband UVB therapy, intense pulsed light (IPL)).

EXAMPLES

The following examples are provided to demonstrate and further illustrate certain preferred embodiments and aspects of the present technology and are not to be construed as limiting the scope thereof.

Example 1

Statin+Cholesterol for Topical Scar Reduction

In this study, efficacy of statin and cholesterol topical treatment in reducing scar was demonstrated in a validated rabbit ear scar model. The rabbit ear scar model was used for this study. Twenty New Zealand White rabbits were divided into two study groups, with six rabbits for 10 µM pravastatin intradermal administration at post-operative day (POD) 15,18 and 21, and fourteen rabbits for 0.4% (9.6 mM), 2% (47.8 mM) and 10% (238.9 mM) simvastatin topical application at POD 14-25. Specimens were collected at 28 days to evaluate the effects of stains on hypertrophic scarring. Treatment with pravastatin intradermal administration significantly reduced scarring when comparing to saline control in term of scar elevation index (SEI). Topical treatment with both medium- and high-dose simvastatin also significantly reduced scarring. High-dose simvastatin topical treatment showed a major effect in scar reduction, but had side effects of scaling, erythema, and epidermal hyperplasia, which were improved with co-application of cholesterol. There is a dose response in scar reduction with low-, medium- and high-dose simvastatin topical treatment. High-dose simvastatin treatment significantly reduced the mRNA expression of CTGF when compared to vehicle control. More directly, high-dose simvastatin treatment also significantly reduced the mRNA expression of Collagen 1A1. In conclusion, topical simvastatin significantly reduces scar formation.

MATERIALS AND METHODS

Statin Preparation and Administration

For intradermal administration, a dose of 100 µl 10 µM pravastatin in phosphate buffered saline (PBS) per healed wound was chosen based on in vitro and in vivo studies[4,11-13], and 3 doses were given at post-operative day (POD) 15, 18 and 21 (Table 1).

Transdermal penetration is the critical limitation in topical application. In general, a statin for topical application should have both high solubility and high permeability or penetration[14-16] with molecular weight less than 500 Daltons[17]. The stratum corneum is hydrophobic and a barrier for any topically applied reagent, and so hydrophobic statins should have increased penetration[18]. Of hydrophobic statins, lovastatin has limited solubility in the vehicle that tested; atorvastatin has relative heavier molecular weight (604 Da)[17,19] and so its penetration is limited. Simvastatin is a hydrophobic statin with a moderate molecular weight (418 Da) and potentially increased penetration capability, and most importantly high solubility in the self-microemulsifying drug delivery system (SMEDDS)[20]. A modified Capmul MCM EP-based microemulsion formulation with Transcutol as cosurfactant was developed for topical delivery of simvastatin with 1:1 (v/v) Capmul MCM EP/Transcutol[21] (herein incorporated by reference its entirety). Dosing schedules were chosen based upon in vitro dosing necessary to interfere with CTGF expression[11-13,22,23], and extrapolated to animal models based upon our experience with dose response curves for growth factors in our rabbit ear model[24].

In order to assess whether simvastatin demonstrates a dose response, effects of low-(0.4%; 9.6 mM), medium-(2%; 47.8 mM) and high-dose (10%; 238.9 mM) simvastatin on scar reduction were explored. Topical statin inhibits synthesis of cholesterol in epidermis, which interferes with the stratum corneum. In previous reports, treated skin developed scale, erythema, and epidermal hyperplasia when statin was used topically[25-27]. Two (2)% cholesterol was co-applied with high-dose simvastatin.

In summary, low-(0.4%), medium-(2%) and high-dose (10%) simvastatin with or without 2% cholesterol were prepared in Transcutol/Capmul MCM EP 1:1(v:v)[21,30-32] for topical application. Daily topical application (10 µl per wound) of above reagents was given on POD 14-25 (Table 1). Transcutol (Diethylene glycol monoethyl ether) was purchased from Sigma-Aldrich (St. Louis, Mo.), and Capmul MCM EP (Glycerol Monocaprylocaprate (Type I)) was kindly gifted by Abitec Corporation (Janesville, Wis.).

Animal Models

The Northwestern University Animal Care and Use Committee approved the use of animals in this study. Twenty New Zealand White rabbits (3-6 months, ~3 kg; Covance Research Products, Inc, Cumberland, Va.) were divided into two study groups, with six rabbits for intradermal injection study, and fourteen rabbits for topical application study. The rabbit ear hypertrophic scar model was made as previously described[33]. Briefly, full-thickness dermal punches were made on the ventral surface of the ear down to but not including the perichondrium. The cartilage was scored around the circumference of the wound to allow for histomorphometric analysis. The wounds were covered with a semi-occlusive dressing Tegaderm (3M Health Care, St.

TABLE 1

| | Treatment Methods | | | | |
|---|---|---|---|---|---|
| | Intradermal 10 µM pravastatin | Topical 0.4% simvastatin | Topical 2% simvastatin | Topical 10% simvastatin | Topical 10% simvastatin/ cholesterol |
| Control | PBS | T/C* with 5% chol | T/C* | T/C* | T/C* with 2% chol |
| Treatment | Statin in PBS | Statin/chol in T/C* | statin in T/C* | statin in T/C* | Statin/chol in T/C* |
| N of Samples | 24 | 9 | 31 | 17 | 17 |

Note:
PBS denotes phosphate buffered saline
*T/C means Transcutol/Capmul MCM EP

Paul, Minn.), which was replaced as needed. Each wound was considered a separate sample because of independent healing and response to treatments.

Tissue Harvest and Histological Analysis

Animals were euthanized at POD 28. Rectangular samples including scar tissue and about 3.5 mm normal skin at each side were harvested. One half of a rectangular biopsy was taken for histological analysis. Tissues underwent routine processing, paraffin embedding, and sectioning. A 4-μm cross section through the center of each rectangular biopsy was taken to approximate the diameter of the scar section to the actual 7 mm diameter. The tissues were stained with hematoxylin & eosin (H&E) and examined under light microscopy. Several histomorphometric measurements were determined using a digital image analysis system (NIS-Elements Basic Research, Nikon Corporation, Kanagawa, Japan) at 2× and 10 magnification as previously described[33]. Each parameter was measured in a blind manner. Scar elevation index (SEI) was calculated to quantify the extent of hypertrophic scarring in the scarring model. Scored nicks in the cartilage served as references of the original wound diameter.

Quantification of CTGF and Collagen 1A1 mRNA Expression

Total RNA was extracted from dermal scar tissue of high-dose simvastatin topical treatment and control scars using TRI reagent (Sigma-Aldrich, St. Louis, Mo.), and contaminated DNA was removed with Turbo DNA-free kit (Ambion, Austin, Tex.). The cDNA was synthesized from one μg of total RNA by superscript II reverse transcriptase (Invitrogen, Grand Island, N.Y.) with 100 ng of random primers in 20 μl of volume. Synthesized cDNA was quantified in a sequence detection system (ABI StepOnePlus; Applied Biosystems, Foster City, Calif.) using SYBR green and specific primers of CTGF and collagen 1A1, and 18 S rRNA was set as endogenous control. The sequence of primers is as followed: CTGF (5'-CTT CTG TCG GCT GGA GAA AC-3' (SEQ ID NO:1) & 5'-TTA GCC CGG TAC GTC TTC AC-3' (SEQ ID NO:2)); Collagen 1A1: (5'-TAA GAG CTC CAA GGC CAA GA-3'(SEQ ID NO:3) & 5'-TGT TCT GAG AGG CGT GAT TG-3' (SEQ ID NO:4)); Glyceraldehyde 3-phosphate dehydrogenase (5'-AGG TCA TCC ACG ACC ACT TC-3' (SEQ ID NO:5) & 5'-GTG AGT TTC CCG TTC AGC TC-3' (SEQ ID NO:6)).

Statistical Analysis

For statistical analysis of histological and molecular analysis results, Student's paired t test was applied to see if there is a difference between treatment and control group, p<0.05 was used as significant. All values were represented as mean±standard error.

RESULTS

Pravastatin Intradermal Administration Reduces Scar Formation

Figure 2:
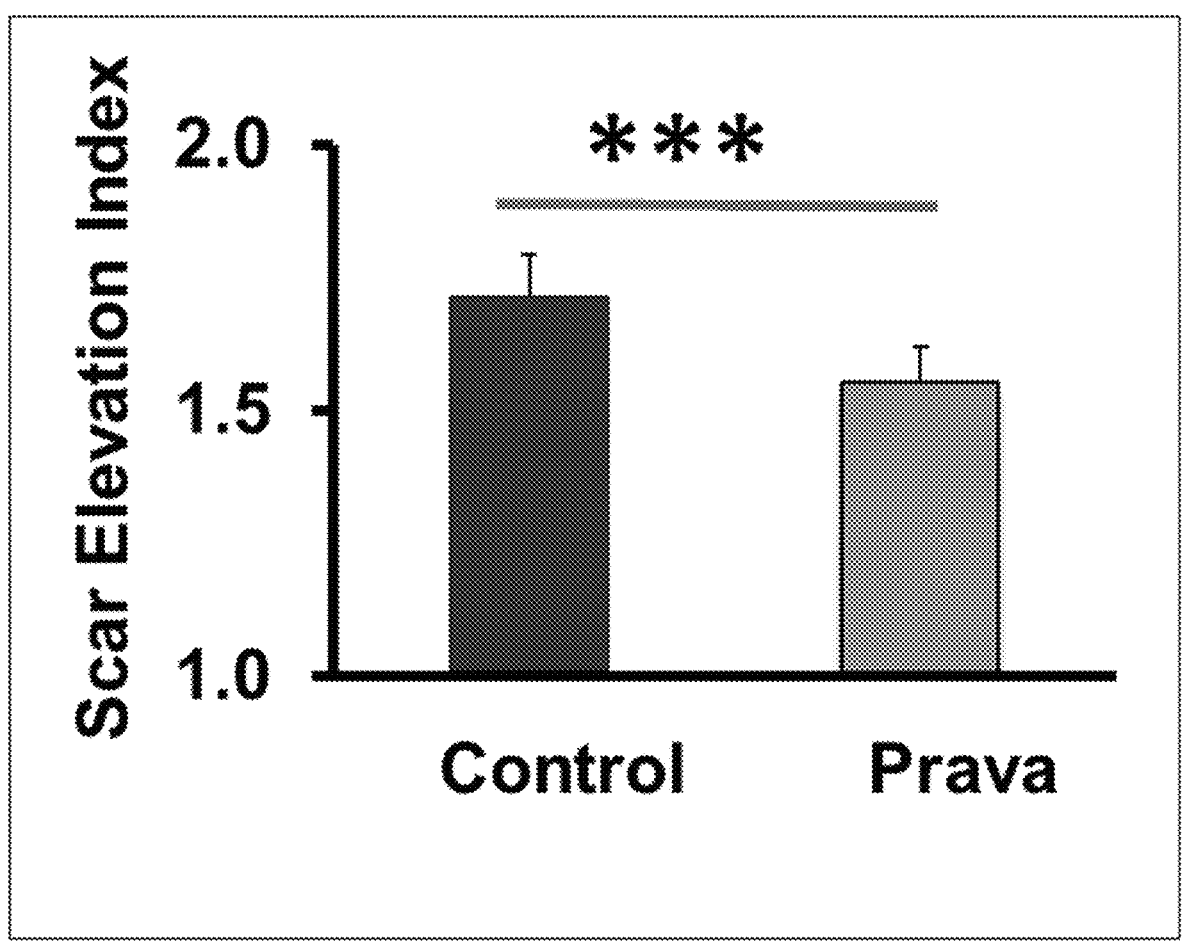
FIG. 2. Pravastatin intradermal treatment reduced hypertrophic scar formation. Pravastatin significantly reduced hypertrophic scarring compared with controls as shown by improvements in SEI.

It was previously reported that local administration of statins by intradermal injection reduced scarring with a concomitant reduction in CTGF expression[4]. There are multiple statins in clinical use including hydrophobic and hydrophilic statins. We confirm the previous report[4] that the hydrophilic statin, pravastatin is effective in reducing scar formation. Treatment with pravastatin intradermal administration significantly reduced scarring when comparing to saline control in term of histological pictures (FIG. 1) and SEI (pravastatin 1.55±0.07 vs saline 1.71±0.08, n=24, p=0.0009, FIG. 2).

Simvastatin Topically Reduces Scarring with the Addition of Cholesterol

Figure 3:
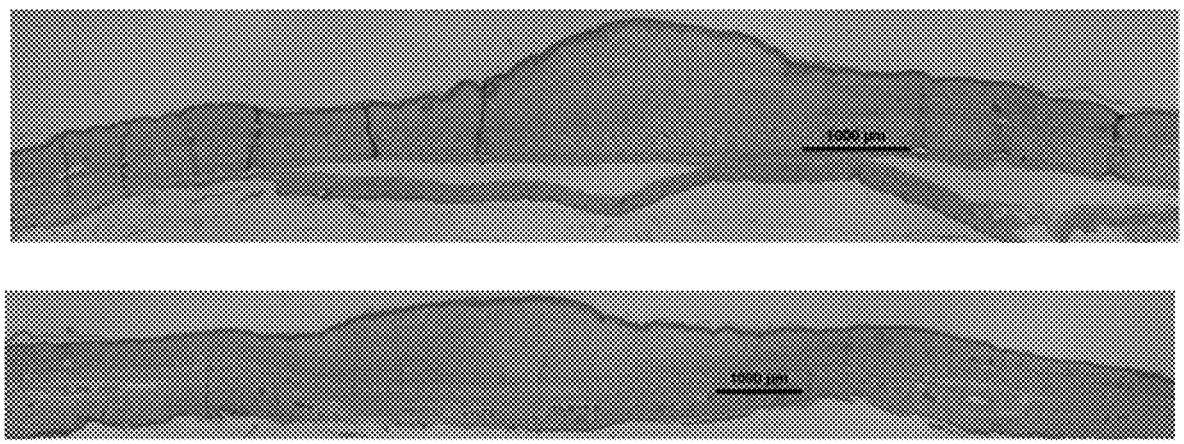
FIG. 3. Low-dose simvastatin topical application (lower picture) did not significantly reduce scarring when comparing to vehicle (upper picture). Representative histological pictures are shown. Bar is 1000 µm in length.
Figure 4:
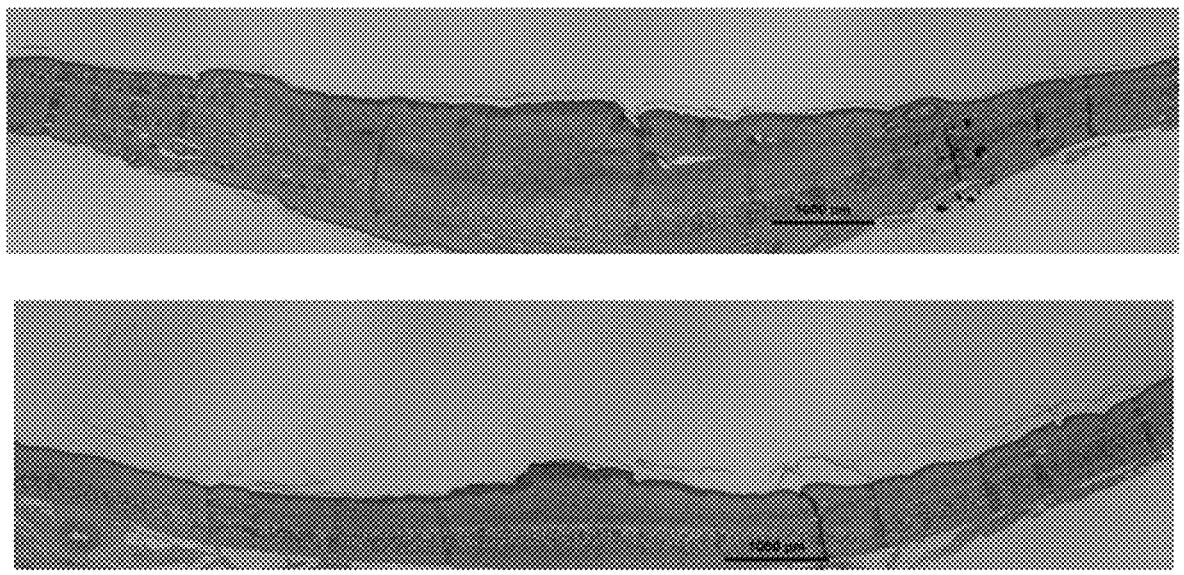
FIG. 4. Medium-dose simvastatin topical application (lower picture) significantly reduced scarring when comparing to vehicle (upper picture). Representative histological pictures are shown. Bar is 1000 µm in length.
Figure 5:
FIG. 5. High-dose simvastatin topical application (lower picture) significantly reduced scarring when comparing to vehicle (upper picture). Representative histological pictures are shown. Bar is 1000 µm in length.
Figure 5:
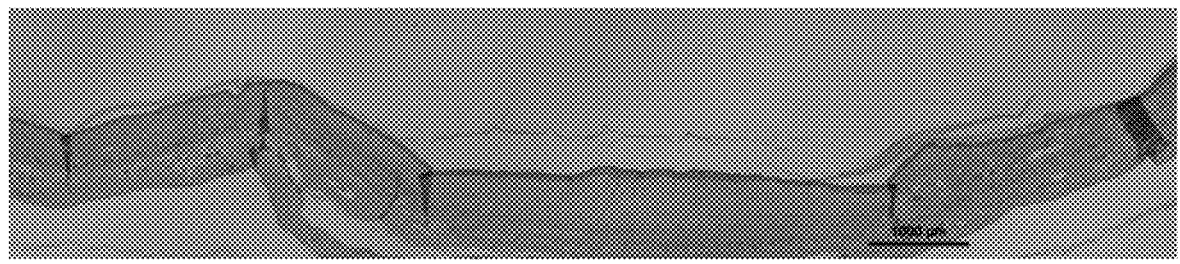
Figure 6:
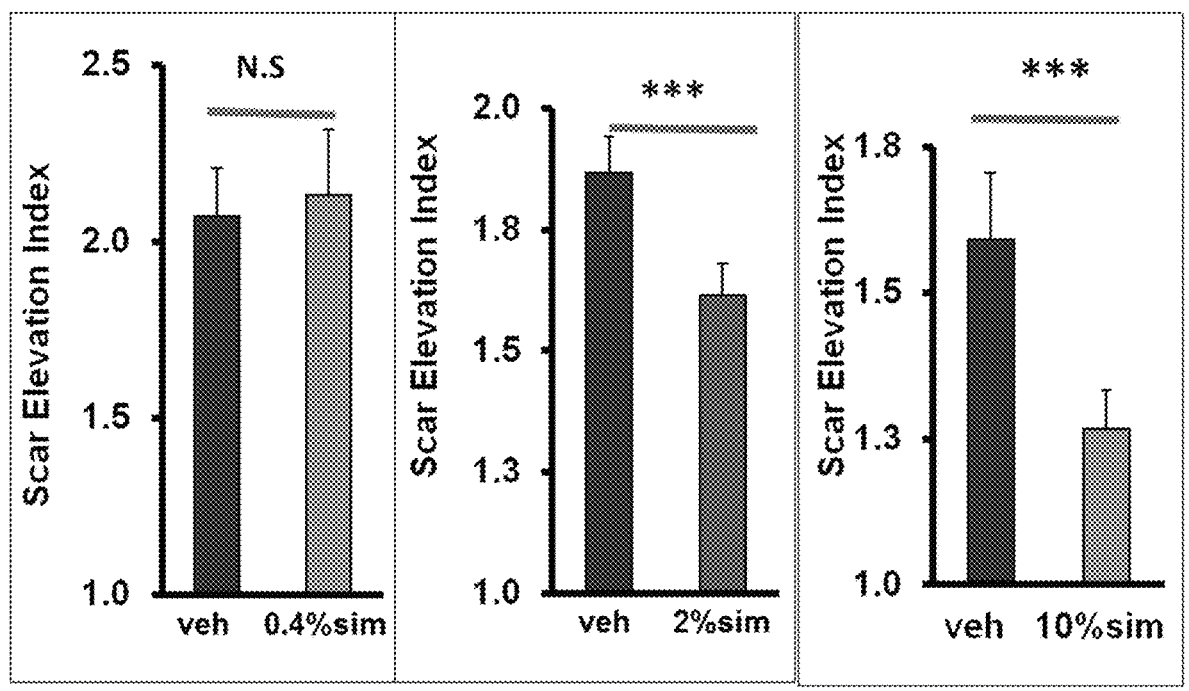
FIG. 6. Effects of simvastatin topical application on hypertrophic scar formation. There is a dose response with low-, medium- and high-dose simvastatin on scar reduction.
Figure 7:
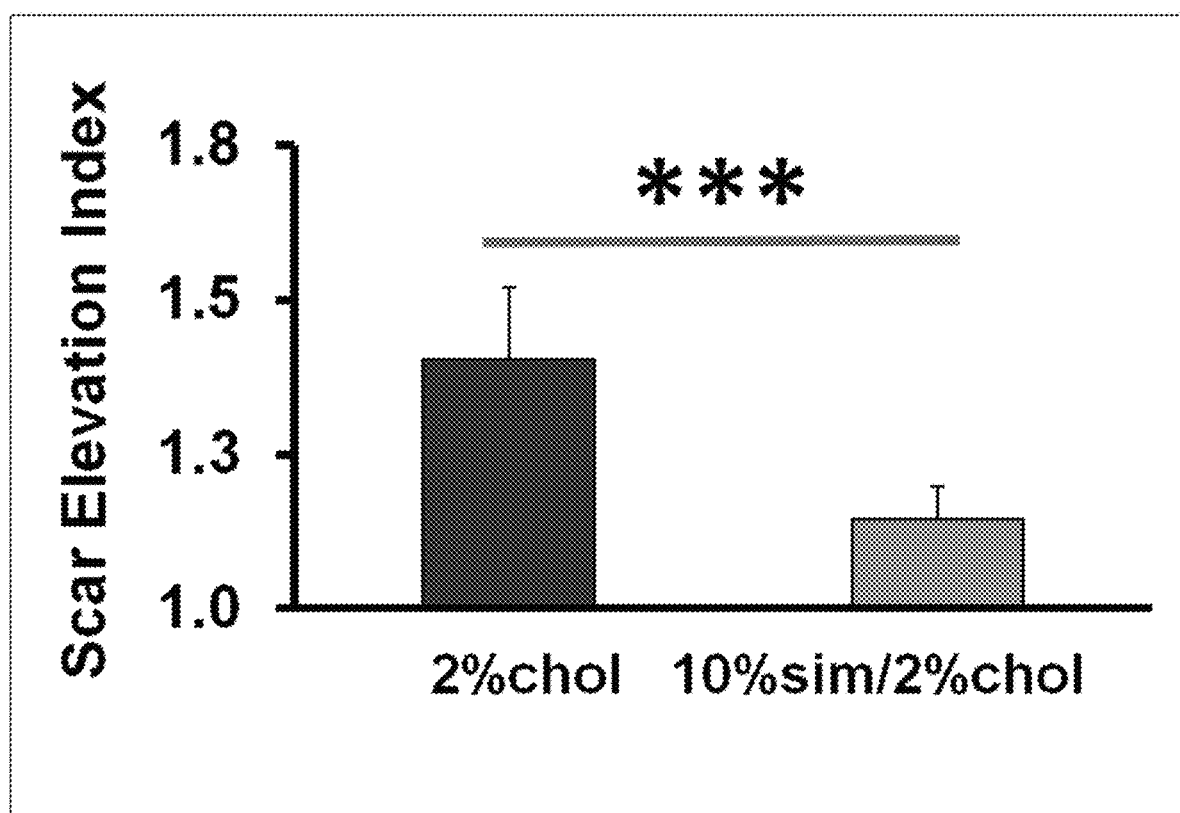
FIG. 7. Simvastatin topical application reduced hypertrophic scar formation. Co-application of high-dose simvastatin with cholesterol significantly reduced hypertrophic scarring compared with controls as shown by improvements in SEI.
Figure 8:
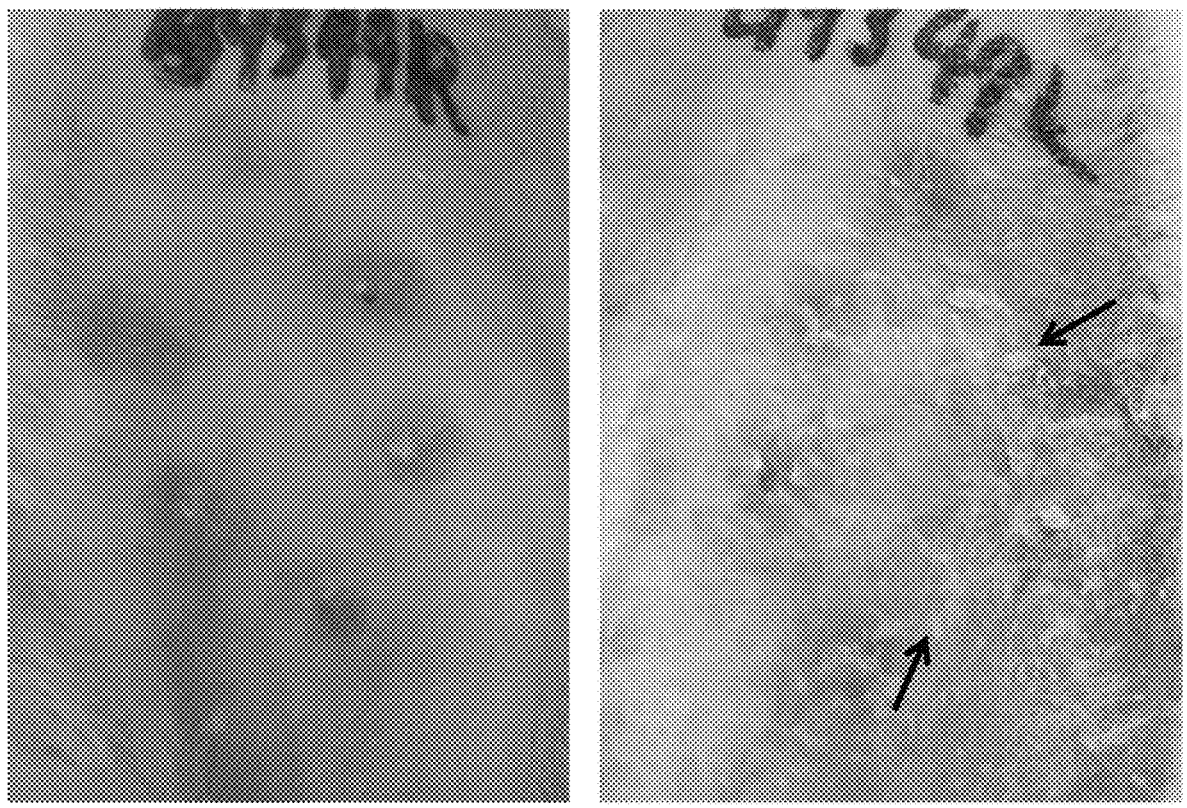
FIG. 8. Some scars with high-dose simvastatin treatment developed scale (arrows, ear at right side), erythema, and epidermal hyperplasia, when comparing with vehicle control (Ear at left side). Representative gross pictures are shown.
Figure 9:
FIG. 9. Scars treated with co-application of high-dose simvastatin with cholesterol developed less scale (arrows, ear at right side), erythema, and epidermal hyperplasia when comparing with high-dose simvastatin treatment alone (Ear at right side in FIG. 7). Vehicle control did not develop scale (Ear at left side). Representative gross pictures are shown.

Topical treatment with low-dose simvastatin did not show scar reduction effect when comparing to vehicle control in terms of histological pictures (FIG. 3) and SEI (simvastatin 2.13±0.19 vs vehicle 2.07±0.14, n=9, p=0.6. FIG. 6). However, topical treatment with both medium- and high-dose simvastatin significantly reduced scarring shown in histological pictures (FIGS. 4 and 5) and SEI (medium-dose 1.61±0.06 vs vehicle 1.87±0.08, n=31, p=0.001; high-dose 1.27±0.07 vs vehicle 1.59±0.11, n=17, p=0.004. FIG. 6). High-dose simvastatin treatment showed a major effect in scar reduction, but had side effects previously reported of visible scaling, erythema, and epidermal hyperplasia (FIG. 8) presumably due to interference with synthesis of cholesterol which is an important component of the stratum corneum. However, vehicle controls didn't show the abnormality. With co-application of cholesterol, high-dose simvastatin treatment also significantly reduced scarring in histological pictures and SEI (co-application 1.14±0.05 vs vehicle 1.40±0.12, n=17, p=0.005. FIG. 7), which is similar to that by high-dose simvastatin treatment only, but with improvement in the scaling, erythema, and epidermal hyperplasia (FIG. 9). Again, vehicle controls didn't show any apparent abnormality. When the high-dose simvastatin groups with and without cholesterol are combined, the significance is even greater (high-dose simvastatin 1.21±0.04 vs vehicle 1.50±0.08, n=34, p=0.00005). In summary, there is a dose response in scar reduction with low-, medium- and high-dose simvastatin topical treatment. Of note, there was mild, not statistically effect of cholesterol on reducing scarring. Treatment with occlusion by a variety of methods[34] reduces scarring, and this is the presumed mechanism for the effect of cholesterol on scarring.

Figure 10:
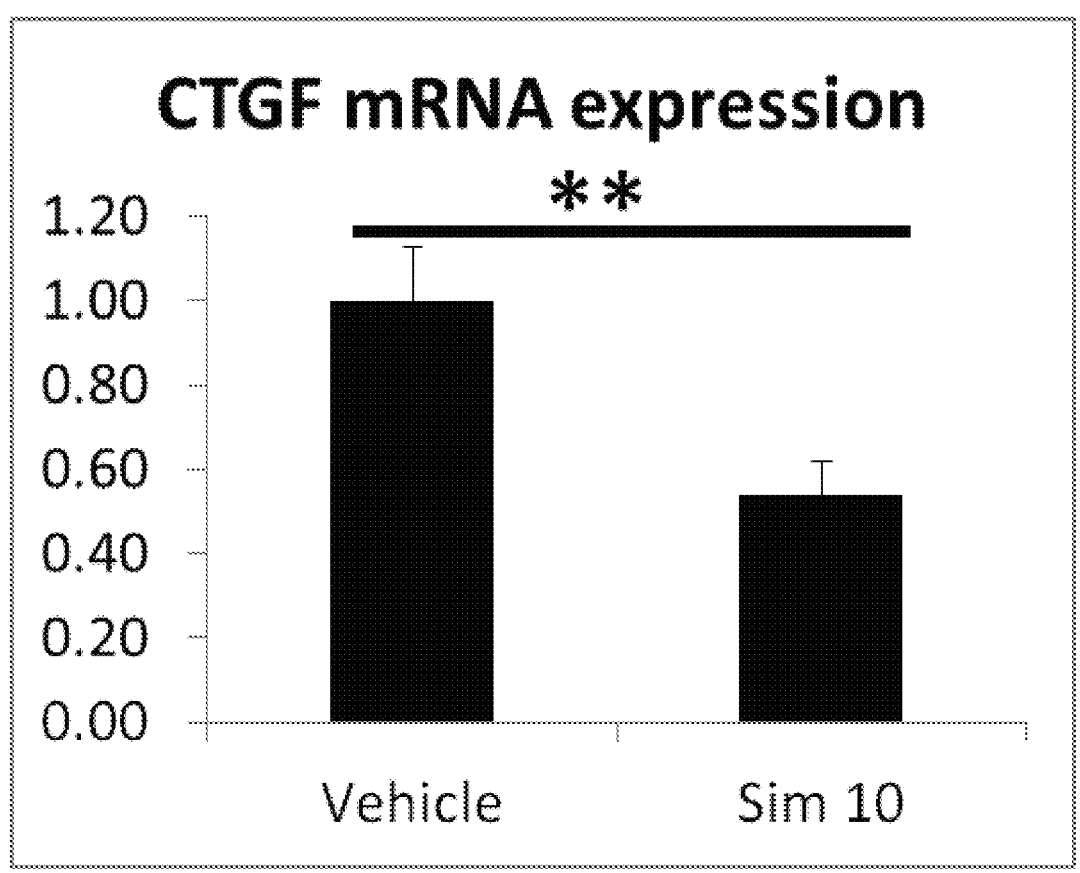
FIG. 10. High-dose simvastatin topical application significantly decreased CTGF mRNA expression.
Figure 11:
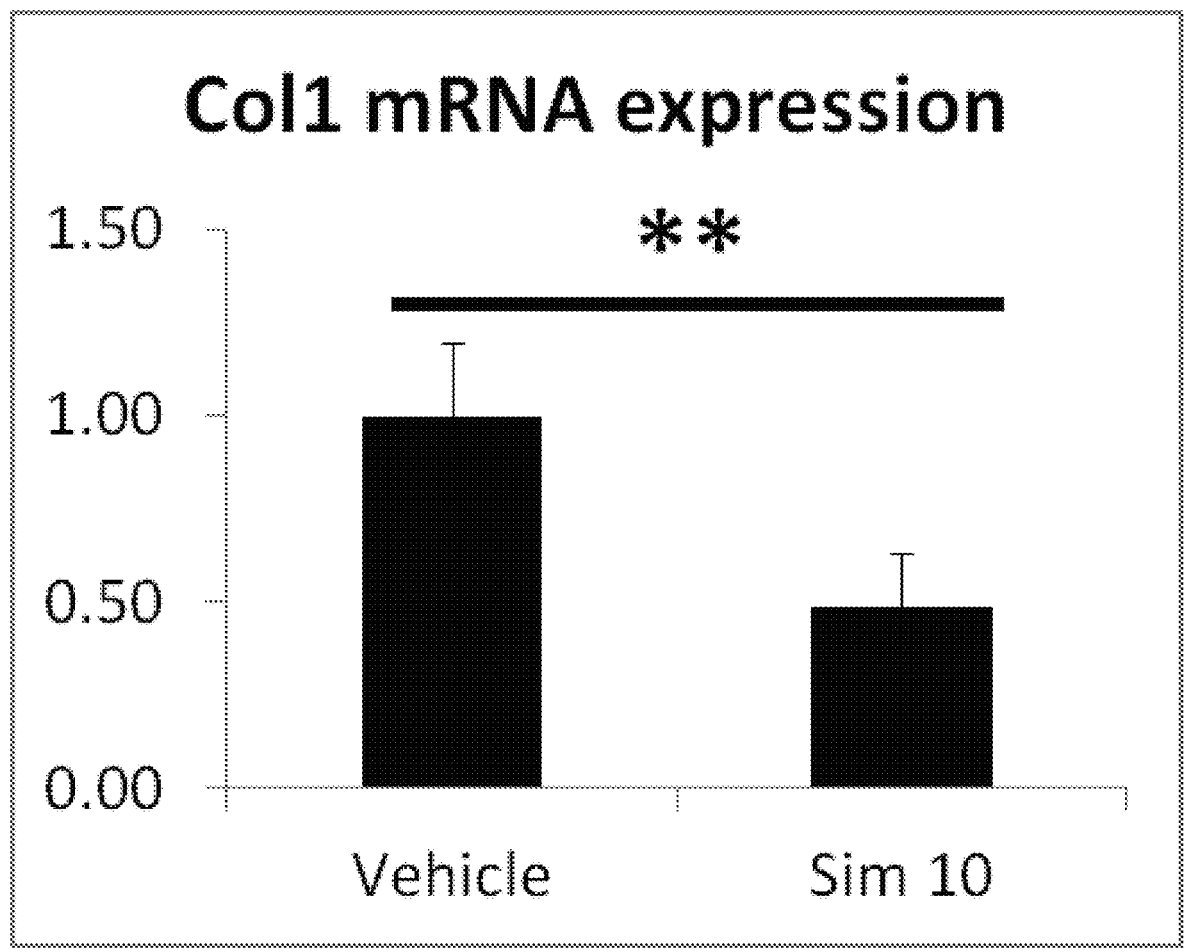
FIG. 11. High-dose simvastatin topical application significantly decreased collagen mRNA expression.

Simvastatin Topical Application Decreases CTGF and Collagen 1A1 mRNA Expression in Hypertrophic Scar Collagen synthesis is regulated by connective tissue growth factor (CTGF) which is a downstream effector of TGFβ, and high expression of CTGF may maintain a fibrotic phenotype[35]. Our previous work had demonstrated that statin interferes with CTGF mRNA expression[4] confirming previous in vitro observations regarding statin[11-13,22,23]. In this Example, high-dose simvastatin treatment significantly reduced the mRNA expression of CTGF to 53.8±8.0% (p<0.01, n=12) when compared to vehicle control. More directly, high-dose simvastatin treatment also significantly reduced the mRNA expression of Collagen 1A1 to 48.5±14% (p<0.01, n=12). Data are presented as mean±SEM (FIGS. 10 and 11). The mechanism of efficacy for statin treatment through interference with CTGF mRNA expression was confirmed.

It was previously reported that intradermal administration of statins could significantly reduce hypertrophic scarring[4]. In addition to further confirming the finding here, we report that topical application of a hydrophobic statin reduces scarring in this study. We utilized a microemulsion system as vehicle for statin topical application with combination of Transcutol as a surfactant and Capmul MCM EP as an oil base.

As the results showed, both medium- and high-dose simvastatin treatment significantly reduced scarring with the latter having more dramatic effect. However, high-dose also caused apparent side effects such as scale, erythema, and epidermal hyperplasia in some cases (FIG. 8). Although surfactant has been reported to cause scaling[36], it is unlikely the case in this Example because vehicle controls with surfactant did not show those side effects, so they should be local side effects from topical high-dose statin treatment[37]. Co-applied cholesterol could moderately override scaling effect caused by simvastatin[25] (FIG. 9). It is unclear if cholesterol plays a direct or indirect role in this finding[29]. The existence of the dose response among low-, medium- and high-dose simvastatin treatments further validated the effect of simvastatin topical treatment on scar reduction.

CTGF is an important downstream mediator of TGF-β, which regulates collagen synthesis without major effects on inflammatory cells, and has been demonstrated to specifically modulate scarring[35]. CTGF overexpression is reported in some pro-fibrotic condition such as scleroderma[38] etc. After injury, it continues to rise steadily through day 40, and blockade of CTGF mRNA by antisense oligonucleotides is associated with reduction of types I and III collagen, and scar reduction[35]. Our results indicate that the scar reduction effect of statin is at least partly through the decrease of CTGF mRNA expression, and consequently the decrease of collagen mRNA expression, which is consistent with Mun's in vitro study[39] and Watts' in vivo study[12]. Whether statin affected the expression of TGF-βRII is unclear in this Example[40]. Furthermore, biphasic effects of simvastatin on host cells have been noted in in vitro experiments where high doses of statins induced cell apoptosis and inversely inhibited angiogenesis[41-43].

As a modern drug carrier system, microemulsions are generally defined as single optically isotropic and thermodynamically stable solutions with droplet sizes in the submicron range. In general, they are composed of an oil phase, a surfactant, a cosurfactant, and an aqueous phase. The core benefits offered by microemulsions include improvement in drug solubility and release, enhanced penetration and bioavailability[44]. Additional benefits have been reported such as ease of manufacturing, less inter- and intra-individual variability in drug pharmacokinetics, and a long shelf life[21,44-46]. Transcutol (Transcutolylene glycol monoethyl ether, 2-(2-Ethoxyethoxy)ethanol) is a non-ionic surfactant and is widely used dissolvent with powerful solubilizing ability[44]. It is reported to increase the permeability of the drugs[46,47], and is listed in the FDA Inactive Ingredient Database for topical use[48]. Capmul MCM EP (Mono/diglycerides of capric acid) is an emulsifier and natural lipophilic surfactant enhancer, and helps to dissolve hydrophobic substances with good solubilizing ability[44]. In addition, it improves permeation[14] and is also listed in the FDA Inactive Ingredient Database[49]. A mixture of Transcutol and Capmul MCM EP was chosen for topical statin treatment in this study[50-55].

Hypertrophic scarring is a multifactorial subacute process extending over months. Underlying genetics and tension on the scar play important roles in excessive scarring. Another important factor is extended or chronic inflammation due to a variety of causes including delayed healing, epithelial barrier dysfunction, and excess bacteria. Prevention of scarring includes surgical and wound treatment methods to minimizing scarring and relieve tension, but therapies to interfere with collagen accumulation are appealing potential therapeutic targets.

REFERENCES

1. Mustoe et al. International clinical recommendations on scar management. Plastic and reconstructive surgery 2002; 110:560-71.
2. Sidgwick et al., A comprehensive evidence-based review on the role of topicals and dressings in the management of skin scarring. Archives of dermatological research 2015; 307:461-77.
3. Gurtner et al. Improving cutaneous scar formation by controlling the mechanical environment: large animal and phase I studies. Annals of surgery 2011; 254:217-25.
4. Ko et al., HMG-CoA reductase inhibitors (statins) reduce hypertrophic scar formation in a rabbit ear wounding model. Plastic and reconstructive surgery 2012; 129:252e-61e.
5. Subedi et al., Recent advances in transdermal drug delivery. Archives of pharmacal research 2010; 33:339-51.
6. Asai et al. Topical simvastatin accelerates wound healing in diabetes by enhancing angiogenesis and lymphangiogenesis. The American journal of pathology 2012; 181:2217-24.
7. Germershausen et al., Tissue selectivity of the cholesterol-lowering agents lovastatin, simvastatin and pravastatin in rats in vivo. Biochemical and biophysical research communications 1989; 158:667-75.
8. Hughes et al., A comparison between the effects of hydrophobic and hydrophilic statins on osteoclast function in vitro and ovariectomy-induced bone loss in vivo. Calcified tissue international 2007; 81:403-13.
9. Ichihara and Satoh Disparity between angiographic regression and clinical event rates with hydrophobic statins. Lancet 2002; 359:2195-8.
10. Fukami et al. Effects of HMG-CoA reductase inhibitors on skeletal muscles of rabbits. Research in experimental medicine Zeitschrift fur die gesamte experimentelle Medizin einschliesslich experimenteller Chirurgie 1993; 193:263-73.
11. Watts et al., RhoA signaling modulates cyclin D1 expression in human lung fibroblasts; implications for idiopathic pulmonary fibrosis. Respiratory research 2006; 7:88.
12. Watts and Spiteri Connective tissue growth factor expression and induction by transforming growth factor-beta is abrogated by simvastatin via a Rho signaling mechanism. American journal of physiology Lung cellular and molecular physiology 2004; 287:L1323-32.
13. Watts et al., Simvastatin inhibits growth factor expression and modulates profibrogenic markers in lung fibroblasts. American journal of respiratory cell and molecular biology 2005; 32:290-300.
14. Shah et al., Preclinical formulations: insight, strategies, and practical considerations. AAPS PharmSciTech 2014; 15:1307-23.
15. Dahan and Miller The solubility-permeability interplay and its implications in formulation design and development for poorly soluble drugs. The AAPS journal 2012; 14:244-51.
16. Petyaev I M. Improvement of hepatic bioavailability as a new step for the future of statin. Archives of medical science: AMS 2015; 11:406-10.
17. Finnin B C, Morgan T M. Transdermal penetration enhancers: applications, limitations, and potential. Journal of pharmaceutical sciences 1999; 88:955-8.
18. Schmalfuss et al., Modification of drug penetration into human skin using microemulsions. Journal of Controlled Release 1997; 46:279-85.
19. Elnaggar et al., Lecithin-based nanostructured gels for skin delivery: an update on state of art and recent applications. Journal of controlled release: official journal of the Controlled Release Society 2014; 180:10-24.
20. Murtaza et al., Solubility enhancement of simvastatin: a review. Acta poloniae pharmaceutica 2012; 69:581-90.
21. Solanki et al., Microemulsion drug delivery system: for bioavailability enhancement of ampelopsin. ISRN pharmaceutics 2012; 2012:108164.

22. Meyer-Ter-Vehn et al., Lovastatin inhibits TGF-beta-induced myofibroblast transdifferentiation in human tenon fibroblasts. Investigative ophthalmology & visual science 2008; 49:3955-60.

23. Eberlein et al., Rho-dependent inhibition of the induction of connective tissue growth factor (CTGF) by HMG CoA reductase inhibitors (statins). British journal of pharmacology 2001; 133:1172-80.

24. Mustoe et al., Growth factor-induced acceleration of tissue repair through direct and inductive activities in a rabbit dermal ulcer model. The Journal of clinical investigation 1991; 87:694-703.

25. Feingold et al., Cholesterol synthesis is required for cutaneous barrier function in mice. The Journal of clinical investigation 1990; 86:1738-45.

26. Feingold et al., The lovastatin-treated rodent: a new model of barrier disruption and epidermal hyperplasia. The Journal of investigative dermatology 1991; 96:201-9.

27. Menon et al., Structural basis for the barrier abnormality following inhibition of HMG CoA reductase in murine epidermis. The Journal of investigative dermatology 1992; 98:209-19.

28. Paller et al. Pathogenesis-based therapy reverses cutaneous abnormalities in an inherited disorder of distal cholesterol metabolism. The Journal of investigative dermatology 2011; 131:2242-8.

29. Murota et al. Topical cholesterol treatment ameliorates hapten-evoked cutaneous hypersensitivity by sustaining expression of 11beta-HSD1 in epidermis. Experimental dermatology 2014; 23:68-70.

30. Inugala et al. Solid self-nanoemulsifying drug delivery system (S-SNEDDS) of darunavir for improved dissolution and oral bioavailability: In vitro and in vivo evaluation. European journal of pharmaceutical sciences: official journal of the European Federation for Pharmaceutical Sciences 2015; 74:1-10.

31. Yadav et al., Development, characterization, and pharmacodynamic evaluation of hydrochlorothiazide loaded self-nanoemulsifying drug delivery systems. TheScientificWorldJournal 2014; 2014:274823.

32. Alinaghi et al., Impact of solidification on the performance of lipid-based colloidal carriers: oil-based versus self-emulsifying systems. Current drug delivery 2015; 12:16-25.

33. Jia et al. Intravenous curcumin efficacy on healing and scar formation in rabbit ear wounds under nonischemic, ischemic, and ischemia-reperfusion conditions. Wound repair and regeneration: official publication of the Wound Healing Society [and] the European Tissue Repair Society 2014; 22:730-9.

34. O'Shaughnessy et al., Homeostasis of the epidermal barrier layer: a theory of how occlusion reduces hypertrophic scarring. Wound repair and regeneration: official publication of the Wound Healing Society [and] the European Tissue Repair Society 2009; 17:700-8.

35. Sisco et al. Antisense inhibition of connective tissue growth factor (CTGF/CCN2) mRNA limits hypertrophic scarring without affecting wound healing in vivo. Wound repair and regeneration: official publication of the Wound Healing Society [and] the European Tissue Repair Society 2008; 16:661-73.

36. Fulmer and Kramer. Stratum corneum lipid abnormalities in surfactant-induced dry scaly skin. The Journal of investigative dermatology 1986; 86:598-602.

37. Brazzelli et al., Effects of systemic treatment with statins on skin barrier function and stratum corneum water-holding capacity. Dermatology 1996; 192:214-6.

38. Leask et al., Insights into the molecular mechanism of chronic fibrosis: the role of connective tissue growth factor in scleroderma. The Journal of investigative dermatology 2004; 122:1-6.

39. Mun et al., Simvastatin inhibits transforming growth factor-beta1-induced expression of type I collagen, CTGF, and alpha-SMA in keloid fibroblasts. Wound repair and regeneration: official publication of the Wound Healing Society [and] the European Tissue Repair Society 2014; 22:125-33.

40. Shang et al., Simvastatin downregulates expression of TGF-betaRII and inhibits proliferation of A549 cells via ERK. Tumour biology: the journal of the International Society for Oncodevelopmental Biology and Medicine 2015; 36:4819-24.

41. Zhu et al. Disparate effects of simvastatin on angiogenesis during hypoxia and inflammation. Life sciences 2008; 83:801-9.

42. Urbich et al., Double-edged role of statins in angiogenesis signaling. Circulation research 2002; 90:737-44.

43. Weis et al., Statins have biphasic effects on angiogenesis. Circulation 2002; 105:739-45.

44. Pathak et al., Role of mucoadhesive polymers in enhancing delivery of nimodipine microemulsion to brain via intranasal route. Acta pharmaceutica Sinica B 2014; 4:151-60.

45. Kogan and Garti. Microemulsions as transdermal drug delivery vehicles. Advances in colloid and interface science 2006; 123-126:369-85.

46. Lawrence and Rees. Microemulsion-based media as novel drug delivery systems. Advanced drug delivery reviews 2000; 45:89-121.

47. Lee et al. Enhanced topical delivery of tacrolimus by a carbomer hydrogel formulation with transcutol P. Drug development and industrial pharmacy 2016:1-7.

48. Sullivan et al., A review of the nonclinical safety of Transcutol(R), a highly purified form of diethylene glycol monoethyl ether (DEGEE) used as a pharmaceutical excipient. Food and chemical toxicology: an international journal published for the British Industrial Biological Research Association 2014; 72:40-50.

49. ABITEC Corporation. Pharmaceutical Regulatory Chart. http://www.abiteccorp.com/wpcontent/files_mf/1380908873ABITECLipidExcipients.PharmaRegulatoryChart2.pdf. Accessed Jan. 28, 2016.

50. Mostafa et al., Transdermal microemulsions of Boswellia carterii Bird: formulation, characterization and in vivo evaluation of anti-inflammatory activity. Drug delivery 2015; 22:748-56.

51. Duangjit et al., Application of Design Expert for the investigation of capsaicin-loaded microemulsions for transdermal delivery. Pharmaceutical development and technology 2015:1-8.

52. Goyal et al., Formulation design and evaluation of a self-microemulsifying drug delivery system of lovastatin. Acta Pharm 2012; 62:357-70.

53. Rajpoot et al., Anticancer efficacy, tissue distribution and blood pharmacokinetics of surface modified nanocarrier containing melphalan. International journal of pharmaceutics 2012; 426:219-30.

54. Pund et al., Multivariate analysis of physicochemical characteristics of lipid based nanoemulsifying cilostazol-quality by design. Colloids and surfaces B, Biointerfaces 2014; 115:29-36.

55. Cho et al. Development of udenafil-loaded microemulsions for intranasal delivery: in vitro and in vivo evaluations. International journal of pharmaceutics 2012; 423:153-60.

56. Farsaei et al., Potential role of statins on wound healing: review of the literature. International wound journal 2012; 9:238-47.

57. Jowkar and Namazi. Statins in dermatology. International journal of dermatology 2010; 49:1235-43.

58. Fitzmaurice et al., Do statins have a role in the promotion of postoperative wound healing in cardiac surgical patients? The Annals of thoracic surgery 2014; 98:756-64.

59. Suzuki-Banhesse et al. Effect of atorvastatin on wound healing in rats. Biological research for nursing 2015; 17:159-68.

60. Evangelista et al., Simvastatin as a novel therapeutic agent for venous ulcers: a randomized, double-blind, placebo-controlled trial. The British journal of dermatology 2014; 170:1151-7.

61. Laing et al., Effect of pravastatin on experimental diabetic wound healing. The Journal of surgical research 2010; 161:336-40.

62. Toker et al., Topical atorvastatin in the treatment of diabetic wounds. The American journal of the medical sciences 2009; 338:201-4.

63. Bitto et al. Simvastatin enhances VEGF production and ameliorates impaired wound healing in experimental diabetes. Pharmacological research 2008; 57:159-69.

64. Wang et al., Topical simvastatin promotes healing of *Staphylococcus aureus*-contaminated cutaneous wounds. International wound journal 2015.

65. Rego et al. Simvastatin improves the healing of infected skin wounds of rats. Acta cirurgica brasileira/Sociedade Brasileira para Desenvolvimento Pesquisa em Cirurgia 2007; 22 Suppl 1:57-63.

66. Vukelic et al. Farnesyl pyrophosphate inhibits epithelialization and wound healing through the glucocorticoid receptor. The Journal of biological chemistry 2010; 285: 1980-8.

All publications and patents mentioned in the above specification are herein incorporated by reference. Various modifications and variations of the methods and compositions provided herein will be apparent to those skilled in the art without departing from the scope and spirit of the technology. Although the technology has been described in connection with specific preferred embodiments, it should be understood that the technology as claimed should not be unduly limited to such specific embodiments. Indeed, various modifications of the described modes for carrying out the technology that are obvious to those skilled in molecular biology, genetics, physiology, biochemistry, medical science, or related fields are intended to be within the scope of the following claims.

We claim:

1. A method of preventing or reducing scar formation in the skin of a subject during wound healing comprising:
   administering a composition topically to a wound site of a subject such that scar tissue formation in said skin is reduced or prevented during wound healing,
   wherein said administering occurs at least two weeks after said wound site is generated and is repeated daily for at least one week,
   wherein said composition comprises:
   i) a pharmaceutically acceptable carrier,
   ii) a statin at a concentration of 6-10% of said pharmaceutically acceptable carrier, and
   iii) cholesterol, cholesterol derivative, or cholesterol analog at 1-15% of said pharmaceutically acceptable carrier.

2. The method of claim 1, said cholesterol derivative is a cholesterol ester selected from the group consisting of: cholesteryl capronate, cholesteryl pelargonate, cholesteryl caprinate, cholesteryl undecilate, cholesteryl laurate, cholesteryl tridecilate, cholesteryl miristinate, cholesteryl palmitate, and cholesteryl stearate.

3. The method of claim 1, wherein said cholesterol analog is selected from the group consisting of: sitosterol, stigmasterol, fucosterol, spinasterol, campesterol, brassicasterol and ergosterol.

4. The method of claim 1, wherein said statin is selected from the group consisting of: simvastatin, rosuvastatin, lovastatin, cerivastatin, fluvastatin, mevastatin, pitavastatin, and pravastatin.

5. The method of claim 1, wherein said statin has molecular weight less than 500 daltons.

6. The method of claim 1, wherein said wound site comprises at least some scar tissue.

7. The method of claim 1, wherein said composition comprises an emulsion.

8. The method of claim 7, wherein said emulsion comprises an oil-in-water emulsion.

9. The method of claim 7, wherein said emulsion comprises a water-in-oil emulsion.

10. The method of claim 7, wherein said emulsion comprises a surfactant and a solvent.

11. The method of claim 10, wherein said surfactant comprises monoacylglycerols.

12. The method of claim 10, where solvent is selected from the group consisting of: water, polyethylene glycol, oleic acid, and 2-(2-ethoxyethoxy) ethanol.

13. The method of claim 1, wherein said composition comprises a form selected from the group consisting of: a powder, a spray, an ointment, a paste, a cream, a lotion, and a gel.

14. The method of claim 1, wherein said composition comprises vegetable oil.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial sequence
<220> FEATURE:
<223> OTHER INFORMATION: DNA Primer

<400> SEQUENCE: 1
cttctgtcgg ctggagaaac                                              20

<210> SEQ ID NO 2
<211> LENGTH: 20
<212> TYPE: DNA
<213> ORGANISM: Artificial sequence
<220> FEATURE:
<223> OTHER INFORMATION: DNA Primer

<400> SEQUENCE: 2
ttagcccggt acgtcttcac                                              20

<210> SEQ ID NO 3
<211> LENGTH: 20
<212> TYPE: DNA
<213> ORGANISM: Artificial sequence
<220> FEATURE:
<223> OTHER INFORMATION: DNA Primer

<400> SEQUENCE: 3
taagagctcc aaggccaaga                                              20

<210> SEQ ID NO 4
<211> LENGTH: 20
<212> TYPE: DNA
<213> ORGANISM: Artificial sequence
<220> FEATURE:
```

```
<223> OTHER INFORMATION: DNA Primer

<400> SEQUENCE: 4
tgttctgaga ggcgtgattg                                              20

<210> SEQ ID NO 5
<211> LENGTH: 20
<212> TYPE: DNA
<213> ORGANISM: Artificial sequence
<220> FEATURE:
<223> OTHER INFORMATION: DNA Primer

<400> SEQUENCE: 5
aggtcatcca cgaccacttc                                              20

<210> SEQ ID NO 6
<211> LENGTH: 20
<212> TYPE: DNA
<213> ORGANISM: Artificial sequence
<220> FEATURE:
<223> OTHER INFORMATION: DNA Primer

<400> SEQUENCE: 6
gtgagtttcc cgttcagctc                                              20
```